United States Patent
Graumann et al.

(10) Patent No.: US 8,186,231 B2
(45) Date of Patent: May 29, 2012

(54) METHOD AND APPARATUS FOR SCANNING A TEXTILE

(75) Inventors: David Graumann, Portland, OR (US); Mark Yarvis, Portland, OR (US)

(73) Assignee: Intel Corporatioon, Sana Claara, CA (US)

(*) Notice: Subject to any disclaimer, the term of this patent is extended or adjusted under 35 U.S.C. 154(b) by 127 days.

(21) Appl. No.: 12/284,420

(22) Filed: Sep. 22, 2008

(65) Prior Publication Data

US 2010/0071482 A1 Mar. 25, 2010

(51) Int. Cl.
*G01L 1/00* (2006.01)
*G01L 1/26* (2006.01)

(52) U.S. Cl. .................................. 73/862.381

(58) Field of Classification Search ............... 73/862.381–862.391, 760–860
See application file for complete search history.

(56) References Cited

U.S. PATENT DOCUMENTS

| | | | |
|---|---|---|---|
| 4,076,535 A * | 2/1978 | Vander Putten | 430/271.1 |
| 5,503,029 A * | 4/1996 | Tamori | 73/862.046 |
| 6,122,403 A * | 9/2000 | Rhoads | 382/233 |
| 6,350,129 B1 * | 2/2002 | Gorlick | 439/37 |
| 6,697,300 B1 * | 2/2004 | Holt | 367/127 |
| 6,809,462 B2 * | 10/2004 | Pelrine et al. | 310/319 |
| 6,826,968 B2 * | 12/2004 | Manaresi et al. | 73/862.046 |
| 7,023,320 B2 * | 4/2006 | Dvorak | 340/5.53 |
| 7,054,133 B2 * | 5/2006 | Orth | 361/278 |
| 7,352,284 B2 * | 4/2008 | Krill | 340/545.1 |
| 7,559,902 B2 * | 7/2009 | Ting et al. | 600/529 |
| 2002/0121146 A1 | 9/2002 | Manaresi et al. | |
| 2006/0211934 A1 * | 9/2006 | Hassonjee et al. | 600/372 |
| 2007/0073131 A1 * | 3/2007 | Ryu et al. | 600/388 |
| 2007/0123948 A1 * | 5/2007 | Dal Molin | 607/32 |
| 2007/0202765 A1 * | 8/2007 | Krans et al. | 442/301 |
| 2007/0281614 A1 * | 12/2007 | Oliver et al. | 455/41.2 |
| 2007/0284134 A1 * | 12/2007 | Sliepen et al. | 174/251 |
| 2008/0097530 A1 * | 4/2008 | Muccio et al. | 607/3 |
| 2010/0001267 A1 * | 1/2010 | Manning et al. | 257/40 |

FOREIGN PATENT DOCUMENTS

| | | |
|---|---|---|
| WO | 2010033573 A2 | 3/2010 |
| WO | 2010033573 A3 | 7/2010 |

OTHER PUBLICATIONS

International Search Report and Written Opinion received for PCT Patent Application No. PCT/US2009/057129, mailed on Apr. 29, 2010, 11 pages.
Marculescu et al., "Electronic Textiles: A Platform for Pervasive Computing", Proceedings of the IEEE, vol. 91, No. 12, Dec. 2003, pp. 1995-2018.
"Smart Carpet: a Footstep Tracking Interface", 21st International Comference on Advanced Information Networking and Application Workshops, IEEE, May 21-23, 2007, vol. 2, pp. 754-760.
Nakad et al., "Communications in Electronic Textile Systems", In Proceedings of the 2003 International Conference on Communications in Computing, 2003, 7 pages.

* cited by examiner

*Primary Examiner* — Max Noori
(74) *Attorney, Agent, or Firm* — Jordan IP Law, PC

(57) ABSTRACT

Some embodiments disclosed herein provide novel approaches for rapidly sensing sense line cross-point interaction in a textile such as a carpet or rug. A textile may comprise transmit and receive sense lines configured so that when an object contacts the textile and depresses one or more transmit lines against one or more receive lines, the object may be detected by monitoring unique signals produced by the transmit sense lines into the receive sense lines to detect the object.

16 Claims, 4 Drawing Sheets

METHOD AND APPARATUS FOR SCANNING A TEXTILE

BACKGROUND

Embodiments disclosed herein relate generally to electronic scanning and in particular, to the electronic scanning of textile surfaces.

Textiles such as rugs, drapes, or carpets can be made for monitoring activity such as human traffic for applications such as security and customer and patient monitoring. Unfortunately, conventional monitoring textiles are limited to smaller surface area applications, for example, using floor mats that employ discrete sensors for each area on a floor surface. Moreover, they tend to be expensive to construct, do not scale well to large surfaces, and have observation densities limited to the physical size of the discrete sensors used for the monitoring. Other approaches employ sensing tiles for large surface areas, but they tend not to have sufficient density for tracking, identifying, or analyzing multiple human occupants, especially in larger areas.

Accordingly, improved approaches may be desired.

BRIEF DESCRIPTION OF THE DRAWINGS

Embodiments of the invention are illustrated by way of example, and not by way of limitation, in the figures of the accompanying drawings in which like reference numerals refer to similar elements.

DETAILED DESCRIPTION

Embodiments disclosed herein provide novel approaches for rapidly sensing sense line cross-point interaction at an update rate that may be suitable for desired human (and animal) tracking and analysis. In some embodiments, signals may be driven onto a first group of sense lines, while a second group are monitored to detect one or more of the signals occurring on lines in the second group. This is done to determine if, and in some cases, to what extent, lines from the first group are interacting with those from the second group caused by activity such as a person or persons walking atop the sense lines.

They may be used for numerous different applications including building security, health monitoring, ubiquitous computing, and communications where textiles containing small embedded scanning chips can be deployed. Furthermore, they may be implemented in textiles used in a wide variety of settings including floor coverings, hung textiles (e.g. light adjusting drapery), held textiles (e.g. haptics), and upholstered items (e.g. an electronic textile couch).

Figure 1:
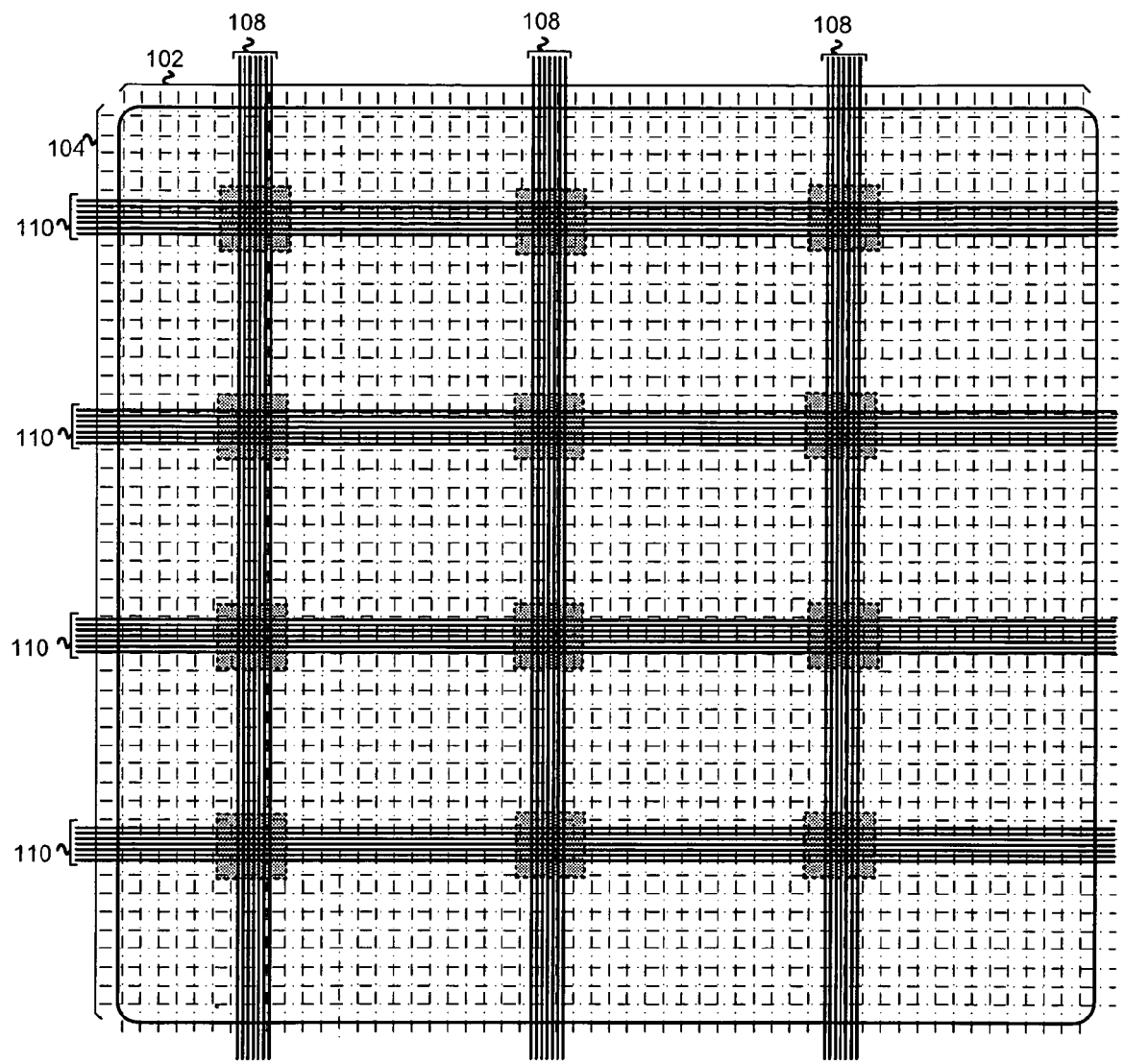
FIG. 1 is a diagram of a textile with sense lines for monitoring activity atop the textile in accordance with some embodiments.

FIG. 1 shows an electronic textile portion in accordance with some embodiments. It is made from numerous threads or yarns (not expressly shown) formed from textile material such as synthetic fiber, wool, cotton, or the like, woven together or otherwise fabricated. Embedded (e.g., woven) within the textile material are first and second groups of spaced apart sense lines, 102 and 104, along with chip lines 108 and 110. In this depiction, the first group of sense lines are in a warp direction, while the second group of lines 104 are in a weft direction. As shown, they cross one another forming numerous "cross-points", which can be monitored by chips to be mounted in the shaded areas, as discussed below. The sense lines may be made from any suitable material such as conductive material, e.g., braided steel yarn that can convey electronic signals for monitoring activity and that can be readily woven (or otherwise formed) within the textile, as is known with current methods. The spacing may be of any suitable dimensions depending on particular design considerations. For example, in some embodiments, they may be spaced in a range from one to three inch intervals apart from one another.

The chip lines 108, 110 are also formed (e.g., woven or otherwise embedded) into the textile to couple off-textile signals, power, and sense lines to the scanning chips (not shown) that will be mounted in the shaded areas. In some embodiments, they are implemented with insulated tinsel wire that can be exposed at desired locations during a manufacturing phase to couple them to the chips, as well as to the sense lines. They may be implemented with braided wire, wire ribbons, or any other suitable material. (It should be appreciated that both the sense and/or chip lines may be woven or otherwise embedded into the textile, or alternatively, may be connected together, e.g., in a loose weave, and attached against a textile or within a separate material such as, for example, within foam to form a pad, e.g., to be placed under the textile.)

Figure 2:
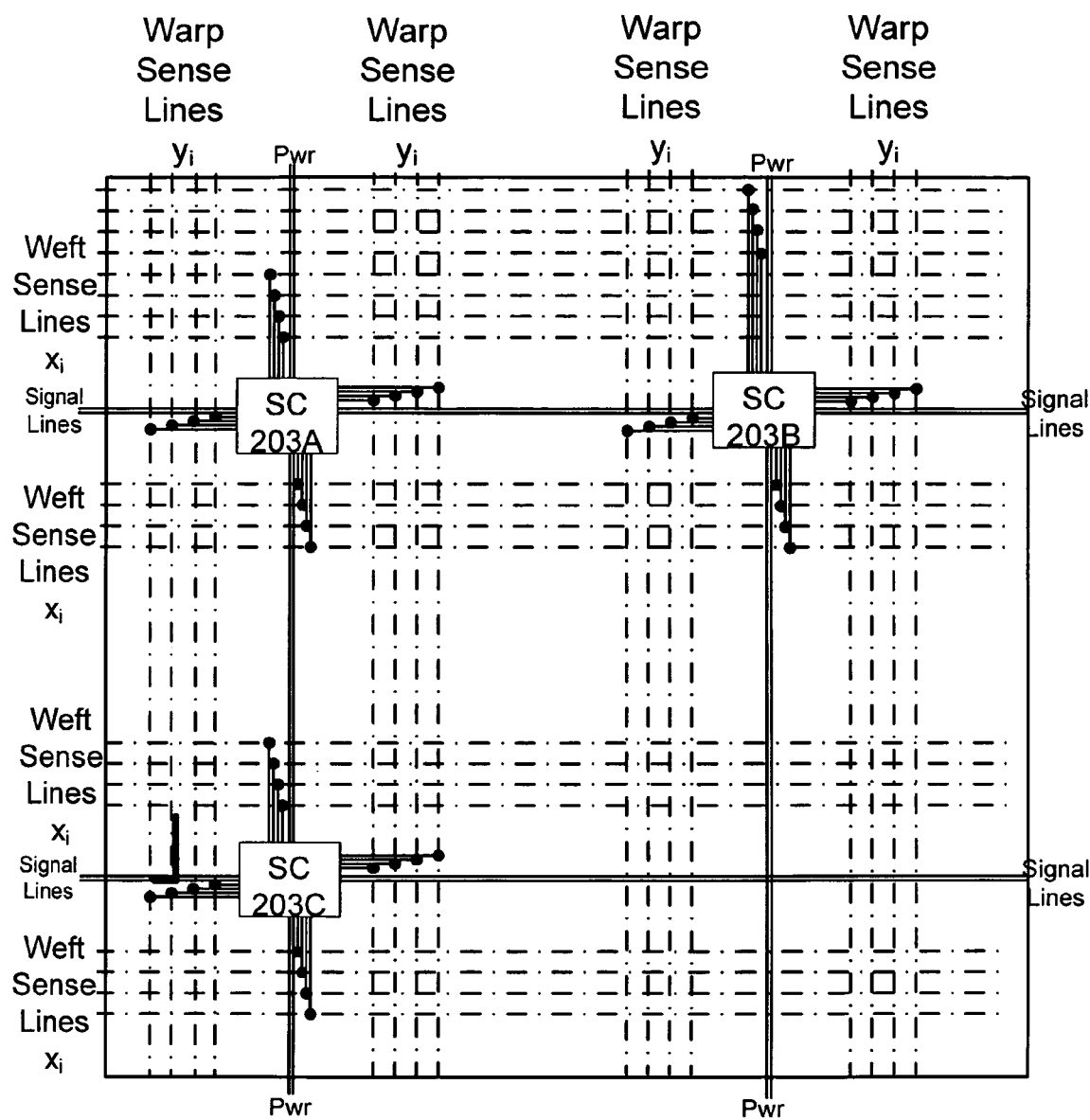
FIG. 2 is a diagram showing embedded monitoring chips in a textile such as the textile of FIG. 1 in accordance with some embodiments.

FIG. 2 is a diagram showing a more detailed portion of the electronic textile from FIG. 1. Shown here are chip lines to couple off-textile power (Pwr) lines, off-textile signal lines (Signal Lines), and warp/weft sense lines to scanning chips 203. (For simplicity sake, only a portion of the textile is shown, and only some of the sense lines and chip lines are shown. Moreover, the open spaces between sense line sections would typically be filled in an actual implementation but appear here for ease of understanding to keep the drawing from becoming too cluttered.) It should be appreciated that in some embodiments, there may be more or less chip lines per scanning chip to connect to the different sense lines. In addition, while separate power (Pwr) and signal (Signal Lines) lines are used, in some embodiments, they may co-exist on the same lines (e.g., DC supply and AC signal sharing common line) or alternatively, signals could be conveyed on/the textile using wireless techniques.

In the depicted embodiment, separate chips (e.g., 203A, 203B, 203C, etc.) are used to monitor separate regions of the textile. For example, each chip could monitor a 3×3 foot region. More chips allow for fewer chip to chip line attachments per chip and faster scanning but may cost more and be less efficient to manufacture and more cumbersome to attach to the textile. Accordingly, appropriate trade-offs may be considered for particular implementations in deciding how many chips to use for scanning.

In some embodiments, the scanning chips 203 are implemented with so-called system on chip (SoC) devices, e.g., chips from the Intel™ EP80579 Integrated Processor family.

The scanning chips 203 are configured to scan the surface for details of surface occupancy. Users walk on the surface and are sensed by the scanning chip circuitry for cross-point connectivity, which results from, e.g., foot pressure atop the cross-point. Cross-point level changes may be analyzed using computer vision methods for gait analysis and occupancy tracking. Conceptually one could liken the electronic textile surface to a large keyboard or touch screen. With embodiments disclosed herein, scanning processing methods are able to sense multiple cross-point hits (or occurrences) on one or more sense lines at the same time, and even though conductive wire can be used for the sense lines to indicate activity when crossing lines touch one another, the degree (or magnitude) to which they contact each other may be assessed, in addition to whether they are or are not in contact with each other.

Figure 3:
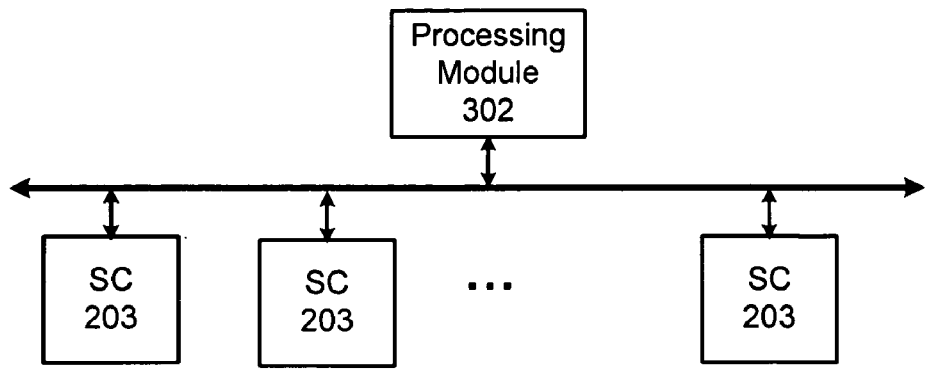
FIG. 3 is a diagram showing a network for monitoring activity atop a textile surface such as that shown in FIGS. 1 and 2 using multiple scanning chips in accordance with some embodiments.

FIG. 3 is a block diagram of a system for accumulating and processing activity data from the different chip regions in a textile. It comprises a processing (e.g., centralized processing) module 302 and scanning chips 203 communicatively linked to the processing module 302. They may be linked to the processing module, which is typically off of the textile, in any suitable way including wired or wireless methods. In some embodiments, each scanning chip 203 scans for cross-point hits and then feeds this information back to the centralized processing module. For example, each scanning chip may send to the centralized module the absolute energy of the received carrier signal (indicating relative degree of cross-point contact, which may be indicative of the force or weight atop the cross-point), the corresponding weft/warp cross-point location, and the time that the cross-point contact was observed. (Note that in other embodiments, higher level scan processing tasks, including identification and tracking tasks, may be performed, e.g., without a central processing unit, on the individual scan chips in a distributed fashion.)

The processing module 302 collects the cross-point activity information over time and constructs an 'image' of the textile surface for high-level analysis. For example, the processing module (or another computing device) may characterize persons based on their foot depression characteristics including foot size, shoe type, weight, gait, and the like. In this way, a unique signature may be derived for individuals. The signature could be associated with the person's actual identity, e.g., when checking into a clinic or dependent-care facility, the person's identity could be associated with their scanned cross-point signature, and the person could then be later identified by matching a monitored signature to their signature in a database. In other applications, actual identity may not be required. For example, the mere presence and/or number of persons entering an area could be tracked. Persons of skill will appreciate that countless other applications using a variety of different identification algorithms from simple to complex may be used and the invention is not so limited.

Figure 4:
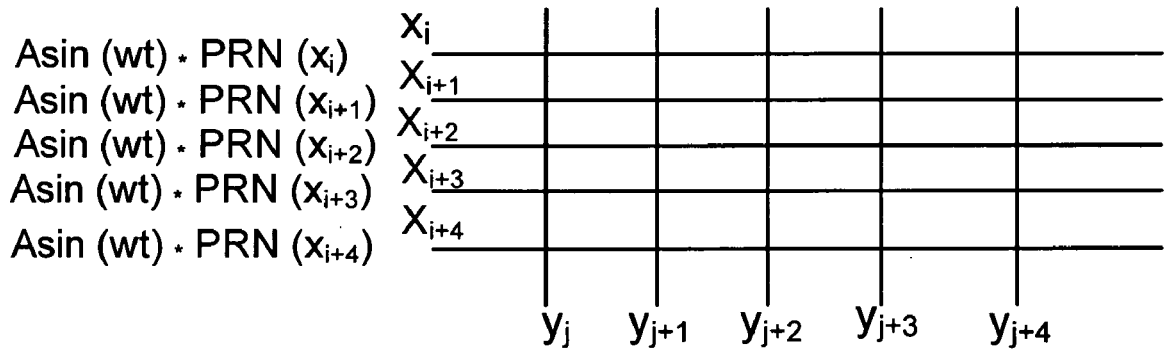
FIG. 4 is a diagram showing a portion of a grid to be scanned in accordance with some embodiments.
Figure 5:
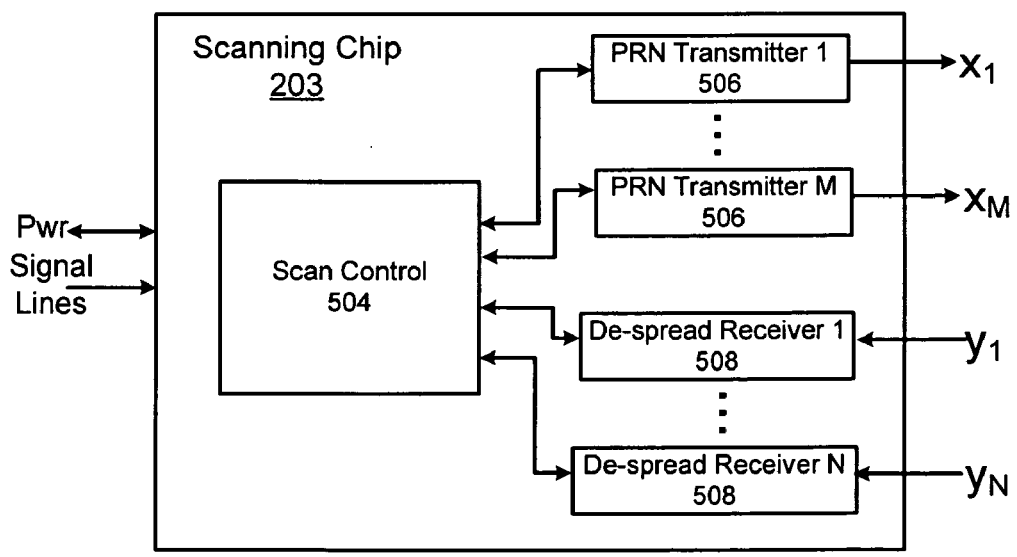
FIG. 5 is a block diagram of a portion of a scanning chip for scanning the grid portion of FIG. 4 in accordance with some embodiments.

FIG. 4 is a conceptual drawing to depict how signals are scanned and monitored by a scanning chip for its region, and FIG. 5 is a block diagram showing a suitable scanning chip for performing these scanning operations. The scanning chip 203 has a scan control block 504, a plurality of transmitters 506 for driving a different, uniquely identifiable, signal onto each transmit sense line ("x" lines here) in the chip's region, and a plurality of de-spreader receivers 508 for scanning each receive sense line ("y" lines here) in the chip's region to determine if one or more of the uniquely identifiable signals is present on the receive (y) lines. These blocks represent functional blocks in the scanning chip, e.g., SoC, microcontroller, processor, ASIC (application specific integrated circuit), etc., that may be implemented with hardware, software, or a combination of both hardware and software in the chip.

Each transmit sense line (x lines) is electrically driven with a single direct sequence spread spectrum signal created in accordance with, e.g., the indicated equations. The signal comprises a carrier (e.g., 250 kHz sinusoidal wave) and a unique pseudo random number (PRN) spreading function. The PRN component is a pseudo random sequence of digital values (e.g., '1s and '0s or as may be more accurate here, '1s and '−1s) multiplied with the carrier wave to generate a sinusoid that flips from in-phase (0 degree phase shift) when the PRN bit is a '1 and out of phase (180 degree phase shift) when the PRN value is a '−1. The rate at which the values change is known as the "chipping rate", which may be greater than but will typically be less than the carrier frequency. For example, a chipping rate of 1250 phase changes every 5 mSec with a carrier frequency of 250 KHz. may be employed.

Ideally, the PRN sequence for each transmit line should be as orthogonal as is possible to each other so that the different signals may suitably be differentiated in the de-spread receivers 508. The longer the PRN sequence, the easier it will be to achieve this goal, but depending on the chipping rate and processing capability, a large PRN sequence length may result in an undesirably slow scan rate, i.e., the time it takes for a scanning chip to scan its associated cross-points for activity. With a higher scan rate, more sophisticated analysis may be performed, for example, characterization pertaining to a person's gate or other motion related characteristics.

Each of the different PRN sequences for each transmit line (x lines) is received and de-spread on each receive line (y lines) sense line. In some embodiments, the de-spreading may be a massively parallelized process in that the de-spreading of each PRN sequence may be performed in parallel on each of the receive sense lines (y lines), with the de-spreaders running in parallel with each other.

Figure 6:
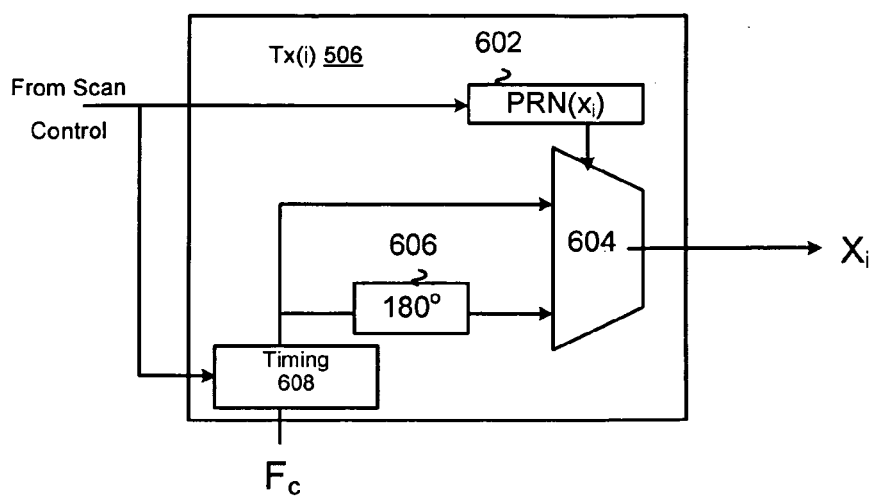
FIG. 6 is a diagram of a scanning transmitter circuit for the circuit of FIG. 5 in accordance with some embodiments.

FIG. 6 is a conceptual diagram of a circuit for implementing a PRN transmitter 506 in accordance with some embodiments. The depicted circuit generally comprises a PRN sequence register 602, a switch (e.g., analog switch 604), a phase inverter 606, and a timing block 608, coupled as shown. The PRN register 602 receives a PRN sequence for its associated transmit (x) line, e.g., from the scan control block 504. It stores the sequence, which is output as a control for the analog switch 604 to select either the in-phase or out-phase version of the carrier frequency ($F_c$) signal, depending on the presently clocked value in the PRN sequence. So, in this example, the chip rate is controlled by the scan control through its control (clocking) of the PRN data out of the PRN register. The scan control block also controls the timing circuit 608 for control of the carrier signal, however, something as simple as a crystal/inverter, with or without delay or tuning, could be used. Regardless, the circuitry for generating the receiver clock ($F_c$) will ideally be used for the transmitting carrier clock, as well. In this way, drift/biases in the transmitter/receiver systems may be made to be negligible without requiring phase and delay lock loops, which avoids the latencies encountered for them to settle before extracting the signal of interest.

Figure 7:
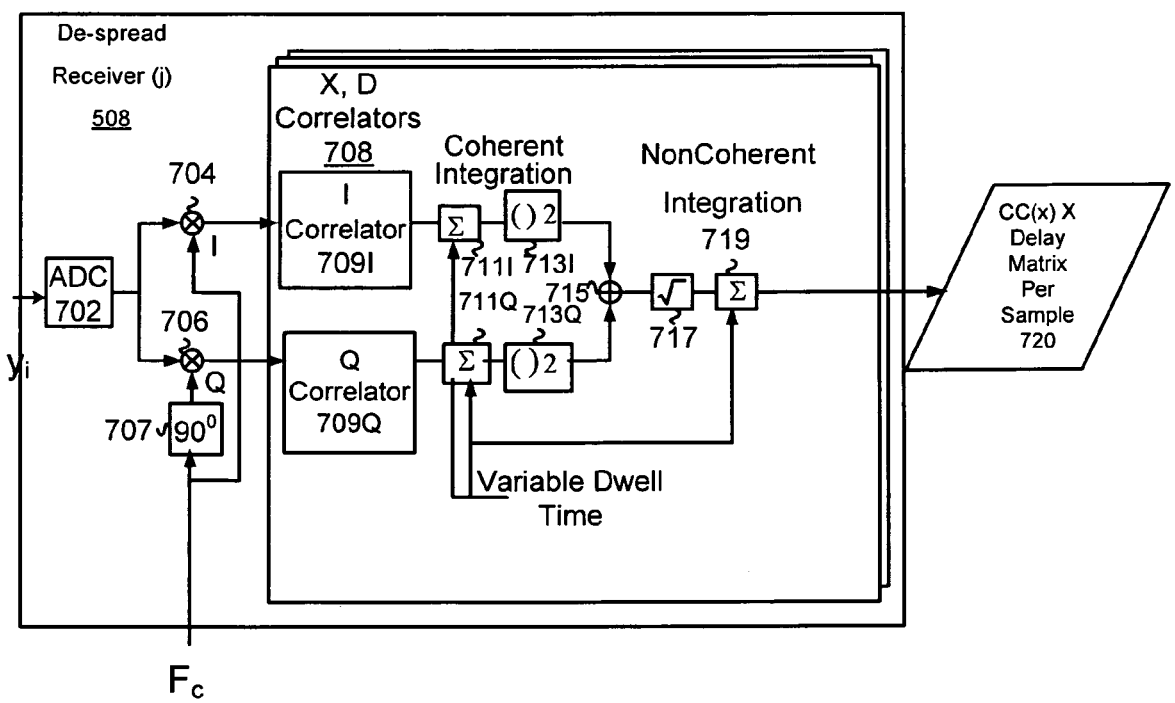
FIG. 7 is a diagram of a scanning receiver for the circuit of FIG. 5 in accordance with some embodiments.

FIG. 7 shows a de-spread receiver 508 in accordance with some embodiments. It is coupled to a receive sense line (y) as its input to receive one or more signals from the different transmit sense lines that may be in contact with its associated line. It generally comprises and A-to-D converter 702, in phase (I) multiplier 704, quadrature phase (Q) multiplier 706, 90 degree phase shifter 707, and correlators 708. The correlators 708 comprise XxD cross-correlators 708 to simultaneously cross correlate the X (number of transmit sense lines in textile) different PRN signals, each at D different delay points against the received signal. (D is the number of different delay points in a PRN sequence, usually the length of the sequence.) Each correlator 708 includes I and Q correlators 709I, Q, a coherent integrator (formed from summing circuits 711I, Q, squaring circuits 713I, Q, and Adder circuit 715), and an non-coherent integrator circuit (formed from a square-root circuit 717 and a summing circuit 719. Thus, for each correlator 708, a unique combination of one of the transmit line PRN sequences and a unique delay point for that PRN sequence are used for correlation with the received, digitized, and I/Q separated signal. The in-phase and quadrature phase correlation components are combined, and the non-coherent correlation peak is tested for an indication of cross-point conductivity. So, for each scan sample, an X by D matrix of correlation results is obtained. These values can then be analyzed to determine if one or more cross-points for the receive line (y) are being activated, and if so, to what extent. A profile can be created showing relative contact strengths for each cross-point, thereby allowing for simple and/or complicated object characterization (e.g., human identification). This analysis may be done in a scan control block on chip or in a suitable processing block off chip.

Additional complexity reduction and processing speed may be achieved by simplifying (if not removing) PRN sequence search algorithms, which can be done because the transmit and receive control circuits may utilize the same crystal and known textile geometries. Furthermore, additional speed up may be achieved by designing the chips and sampling rates to be a multiple of 2 and using block FFT circular correlation methods rather than traditional sequential demodulation schemes.

In the preceding description and following claims, the following terms should be construed as follows: The terms "coupled" and "connected," along with their derivatives, may be used. It should be understood that these terms are not intended as synonyms for each other. Rather, in particular embodiments, "connected" is used to indicate that two or more elements are in direct physical or electrical contact with each other. "Coupled" is used to indicate that two or more elements co-operate or interact with each other, but they may or may not be in direct physical or electrical contact.

The term "PMOS transistor" refers to a P-type metal oxide semiconductor field effect transistor. Likewise, "NMOS transistor" refers to an N-type metal oxide semiconductor field effect transistor. It should be appreciated that whenever the terms: "MOS transistor", "NMOS transistor", or "PMOS transistor" are used, unless otherwise expressly indicated or dictated by the nature of their use, they are being used in an exemplary manner. They encompass the different varieties of MOS devices including devices with different VTs, material types, insulator thicknesses, gate(s) configurations, to mention just a few. Moreover, unless specifically referred to as MOS or the like, the term transistor can include other suitable transistor types, e.g., junction-field-effect transistors, bipolar-junction transistors, metal semiconductor FETs, and various types of three dimensional transistors, MOS or otherwise, known today or not yet developed. The invention is not limited to the embodiments described, but can be practiced with modification and alteration within the spirit and scope of the appended claims. For example, it should be appreciated that the present invention is applicable for use with all types of semiconductor integrated circuit ("IC") chips. Examples of these IC chips include but are not limited to processors, controllers, chip set components, programmable logic arrays (PLA), memory chips, network chips, and the like.

It should also be appreciated that in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

It should be appreciated that example sizes/models/values/ranges may have been given, although the present invention is not limited to the same. As manufacturing techniques (e.g., photolithography) mature over time, it is expected that devices of smaller size could be manufactured. In addition, well known power/ground connections to IC chips and other components may or may not be shown within the FIGS, for simplicity of illustration and discussion, and so as not to obscure the invention. Further, arrangements may be shown in block diagram form in order to avoid obscuring the invention, and also in view of the fact that specifics with respect to implementation of such block diagram arrangements are highly dependent upon the platform within which the present invention is to be implemented, i.e., such specifics should be well within purview of one skilled in the art. Where specific details (e.g., circuits) are set forth in order to describe example embodiments of the invention, it should be apparent to one skilled in the art that the invention can be practiced without, or with variation of, these specific details. The description is thus to be regarded as illustrative instead of limiting.

What is claimed is:

1. A chip, comprising:
   one or more transmit circuits to provide a unique signal to a group of transmit sense lines embedded in a textile; and
   one or more receiver circuits to identify one or more unique signals provided to one or more receive sense lines embedded in the textile to detect an object on the textile, wherein the transmit and receive lines cross over each other to form cross-over points and wherein the location of the object may be determined based on its position relative to one or more of the cross-over points.

2. The chip of claim 1, in which the unique signal comprises a PRN sequence.

3. The chip of claim 1, in which the one or more transmit and receive circuits are clocked via a common crystal.

4. The chip of claim 1, in which the transmit and receive sense lines are disposed relative to each other to form the cross-over points, wherein they conductively couple in accordance with pressure applied to the cross-over points.

5. The chip of claim 1, in which the cross-over points are activated when their associated transmit and receive sense lines contact each other.

6. The chip of claim 1, in which the transmit and receive sense lines are woven into an electronic textile.

7. A method, comprising:
   applying a uniquely identifiable signal to each transmit sense line in a group of transmit sense lines embedded in a textile; and
   monitoring one or more receive sense lines embedded in the textile to determine if one or more of the transmit sense lines is in contact with the one or more receive sense lines, wherein said monitoring includes looking for the uniquely identifiable signals.

8. The method of claim 7, in which the uniquely identifiable signals each comprise a unique PRN sequence.

9. The method of claim 8, in which uniquely identifiable signals are transmitted simultaneously over the group of transmit lines.

10. The method of claim 7, in which all of the uniquely identifiable signals are simultaneously looked for on each of the one or more receive sense lines.

11. The method of claim 7, in which the uniquely identifiable signal's has an energy envelope that is compared against a known transmit signal strength for assessing path loss.

12. An apparatus, comprising:
a textile having transmit sense lines to carry unique signals, and at least one receive sense line to receive the signals from the transmit lines when they contact the at least one receive line to perceive an object on the textile.

13. The apparatus of claim 12, in which the textile comprises a plurality of scan chips to generate the signals for the transmit lines.

14. The apparatus of claim 13, in which the unique signals each have a different PRN encoding.

15. The apparatus of claim 12, in which the at least one receive line is orthogonally disposed relative to the transmit lines.

16. The apparatus of claim 15, in which the at least one receive line comprises a plurality of lines that in combination with the transmit lines make up a sense grid.

* * * * *

UNITED STATES PATENT AND TRADEMARK OFFICE
CERTIFICATE OF CORRECTION

| | | |
|---|---|---|
| PATENT NO. | : 8,186,231 B2 | Page 1 of 1 |
| APPLICATION NO. | : 12/284420 | |
| DATED | : May 29, 2012 | |
| INVENTOR(S) | : David Graumann et al. | |

It is certified that error appears in the above-identified patent and that said Letters Patent is hereby corrected as shown below:

On the cover page, item (73), in column 1, in "Assignee", line 1-2, delete "Intel Corporatioon, Sana Claara, CA (US)" and insert -- Intel Corporation, Santa Clara, CA (US) --, therefor.

On the cover page, item (56), in column 2, under "Other Publications", line 8, delete "Comference" and insert -- Conference --, therefor.

Signed and Sealed this
Seventh Day of August, 2012

David J. Kappos
*Director of the United States Patent and Trademark Office*